US00PP26869P3

(12) United States Plant Patent
Olesen

(10) Patent No.: US PP26,869 P3
(45) Date of Patent: Jun. 28, 2016

(54) MINIATURE ROSE PLANT NAMED 'POULPAL057'

(50) Latin Name: ***Rosa* hybrid**
Varietal Denomination: Poulpal057

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 106 days.

(21) Appl. No.: 14/121,262

(22) Filed: Aug. 15, 2014

(65) Prior Publication Data

US 2016/0050806 P1 Feb. 18, 2016

(51) Int. Cl.
*A01H 5/00* (2006.01)

(52) U.S. Cl.
USPC ..... Plt./118

(58) Field of Classification Search
USPC ..... Plt./118
See application file for complete search history.

(56) References Cited

PUBLICATIONS

PLUTO Plant Variety Database Jan. 23, 2016 p. 1.*

* cited by examiner

*Primary Examiner* — Annette Para

(57) ABSTRACT

A new garden rose plant of the Miniature class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal057'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2008 and the resulting seeds were planted in a controlled environment in Fredensborg, Denmark. The new variety, named 'Poulpal057', originated as a single seedling from the stated cross.

The new variety may be distinguished from its male pollen parent and female seed parent by the following characteristics. The female seed parent is about 25 cm in growth height, while the new variety is 40 cm in growth height. The male pollen parent has apricot flowers while the new variety has yellow flowers.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal057' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulpal057' was selected in the spring of 2009 by the inventor as a single plant from the progeny of the aforementioned hybridization.

Asexual reproduction of 'Poulpal057' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulpal057' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal057'. Specifically illustrated in the drawing are a flower in parts, flower buds, leaves, and stems. Plants shown are 2 years of age.

DETAILED DESCRIPTION OF THE VARIETY

The following is a description of 'Poulpal057',as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulsiana', U.S. Plant Pat. No. 11,638 dated Nov. 21, 2000 are compared to 'Poulpal057' in Chart 1.

CHART 1

| | 'Poulpal057' | 'Poulsiana' |
|---|---|---|
| Petal Count | 50 petals | 15-20 petals |
| Flower Diameter | 65-70 mm | 55-60 mm |
| Colour of petal upper surface after flowers open | Yellow Group 14A | Yellow Group 7B |

FLOWER AND FLOWER BUD

Blooming habit: Continuous.

Flower bud:

*Size*.—Upon opening, 27 mm in length from base of receptacle to end of bud. Bud diameter is 13 mm.

*Bud form*.—Ovoid.

*Bud color*.—As sepals divide petals are Yellow-Green Group 145B and Yellow Group 6C.

*Sepal inner surface*.—Color: Yellow-Green Group 145A. Surface: Lightly pubescent.

*Sepal outer surface*.—Color: Yellow-Green Group 146A with strong intonations of Greyed-Purple Group 183A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—33 mm long, 10 mm wide.

*Receptacle*.—Texture: Smooth. Size: 7 mm in height, 6 mm wide. Color: Yellow-Green Group 144B. Shape: Campanulate.

*Pedicel*.—Surface: Smooth. Length: 35 mm. Diameter: 3 mm on average. Color: Yellow-Green Group 144B with strong intonations of Greyed-Purple Group 183C. Strength: Strong.

Flower bud development: Flower buds are borne singly and in clusters of 3 to 6 flower buds per stem.

Flower bloom:

*Fragrance*.—Moderate floral scent.

*Duration*.—The blooms have a duration on the plant of approximately 14 to 20 days. Petals fall cleanly away from plant after flowers have fully matured.

*Size*.—Flower diameter is 65 to 70 mm when open. Flower depth is 40 mm.

*Flower shape*.—High centered semi double, with a high pointed center which is tightly closed.

*Shape of flower, side view*.—The upper portion is flat. The lower portion is concave.

Petalage: Under normal conditions, flowers have about 50 petals total, 10 of which are petaloids.

General tonality of flower: Open flowers are Yellow Group 13A.

Petal color:

*Upon opening*.—Upper surface: Yellow Group 14A. Lower surface: Yellow Group 15A. Outer petals have light intonations of Orange Group 25C.

*After opening*.—Upper surface: Yellow Group 14A. Lower surface: Yellow Group 13A.

Petals:

*Petal reflex*.—Strong.

*Margin*.—Entire and uniform. No undulations.

*Shape*.—Generally rounded. Apex shape: Rounded. Base shape: Rounded.

*Size*.—30 mm (l)×40 mm (w).

*Texture*.—Smooth.

*Thickness*.—Above average.

Petaloids:

*Size*.—15 mm (l) by 10 mm (w).

*Quantity*.—About 10.

*Shape*.—Irregular. Apex is round, base is acute.

*Color*.—Upper surface: Yellow Group 14A. Lower surface: Yellow Group 15A. Outer petals have light intonations of Orange Group 25C.

Reproductive organs:

*Pollen*.—None observed.

*Anthers*.—Size: 2 to 3 mm in length. Color: Yellow-Green Group 12B. Quantity: 70 on average.

*Filaments*.—Color: Yellow Group 13B. Length: 6 mm.

*Pistils*.—Length: 5 mm. Quantity: 30 on average.

*Stigmas*.—Color: Greyed-Yellow Group 160C.

*Styles*.—Color: Red-Purple Group 58C.

*Location of stigmas*.—Inferior in location relative to the length of the filaments and the height of the anthers.

*Hips*.—None Observed.

PLANT

Plant growth: Upright. Plants are 40 cm in height, and 30 cm wide.

Stems:

*Color*.—Juvenile growth: Yellow-Green Group 146B with strong intonations of Greyed-Purple Group 183B. Mature growth: Yellow-Green Group 146B with light intonations of Greyed-Purple Group 183B.

*Length*.—On average, canes are 30 cm from the base of the plant to the flowering portion.

*Diameter*.—5 mm.

*Internodes*.—On mature canes, there is an average distance of 35 mm between nodes.

*Surface texture*.—Young wood: Smooth. Older wood: Smooth.

Long prickles: None observed.

Plant foliage:

*Compound leaf*.—105 mm (l)×65 (w).

*Quantity*.—3 leaves per 10 cm of stem on average.

*Leaf bearing angle to the stem*.—90 degrees.

*Color of juvenile foliage*.—Upper side: Yellow-Green Group 146B with strong marginal intonations of Greyed-Purple Group 183A. Lower side: Yellow-Green Group 146C with general intonations of Greyed-Purple Group 183C.

*Color of mature foliage*.—Upper side: Yellow-Green Group 146A. Lower side: Yellow-Green Group 146B.

Plant leaves and leaflets:

*Stipules*.—Size: 12 mm long, 3 mm wide. Quantity: 2 per compound leaf. Shape: Linear, slightly broad based with outward extending apices. Margins: Finely serrated. Color: Yellow-Green Group 146A.

*Petiole*.—Length: 18 mm. Diameter: 2 mm.

*Upper surface*.—Color: Yellow-Green Group 144A.

*Lower surface*.—Color: Yellow-Green Group 144B.

*Rachis*.—Length: 30 mm. Upper surface: Color: Yellow-Green Group 144A.

*Lower surface*.—Color: Yellow-Green Group 144B. Observations: Smooth.

*Leaflet*.—Quantity: Normally 5 leaflets. Margins: Serrated. Size: On average terminal leaflets are 45 mm long, 30 mm wide. Shape: Generally elliptical. Base: Rounded. Apex: Cuspidate. Texture: Smooth. Thickness: Average. Arrangement: Odd pinnate. Venation: Reticulate. Glossiness: Not glossy.

Disease resistance: Above average resistance to powdery mildew *Sphaerotheca pannosa,* downy mildew *Peronospora sparsa,* rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpal057', substantially as illustrated and described herein, due to its abundant yellow flowers, disease resistance, and extended period of bloom.

* * * * *

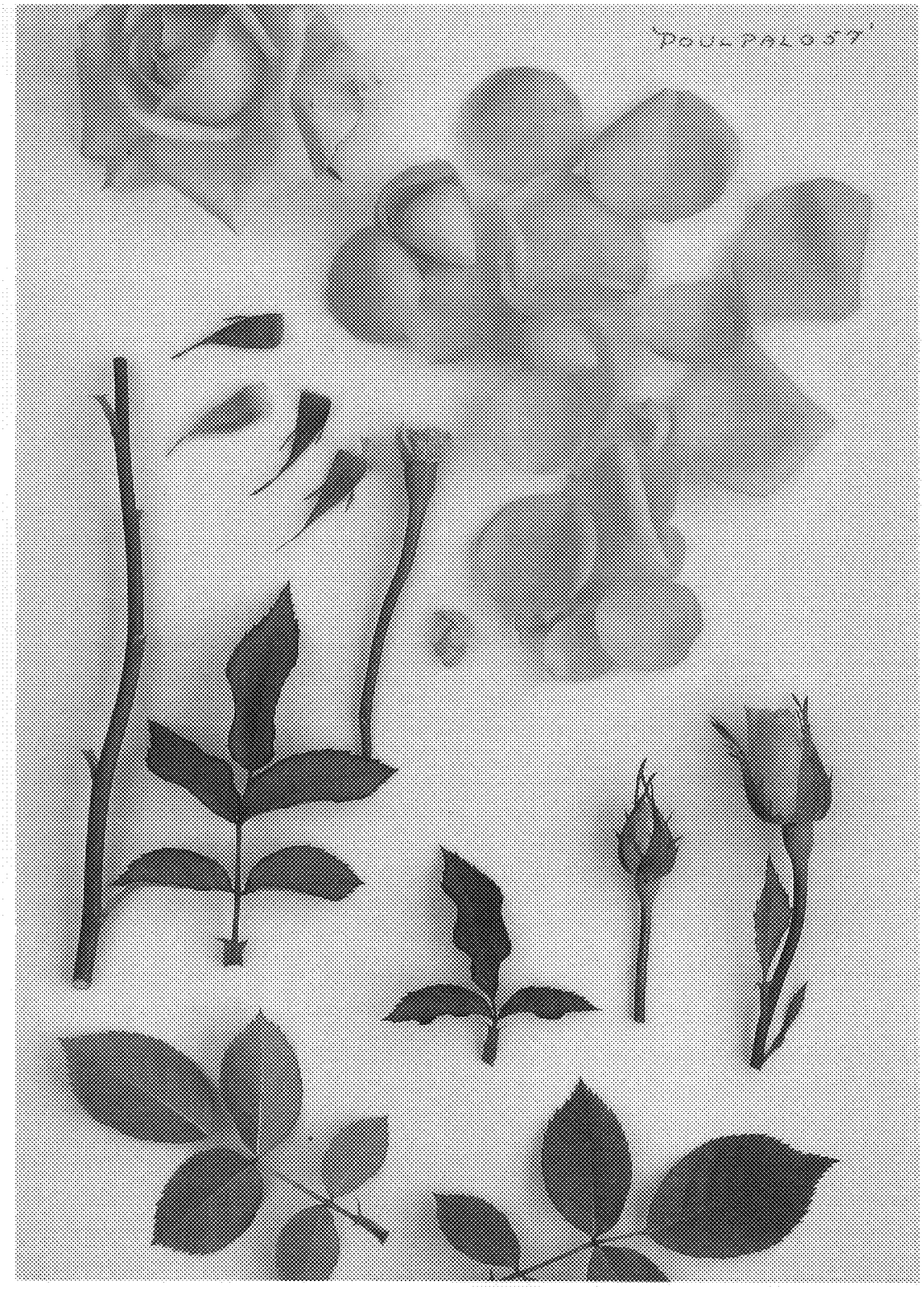
'POULPALO57'